(12) United States Patent
Mettler

(10) Patent No.: US 6,300,512 B1
(45) Date of Patent: Oct. 9, 2001

(54) METHOD FOR PRODUCING A 1-(3-CYCLOPENTENYLOXY-4-ALKOXYPHENYL)-4-OXOCYCLOHEXANECAR-BONITRILE

(75) Inventor: Hans-Peter Mettler, Visp (CH)

(73) Assignee: Lonza AG (CH)

( * ) Notice: Subject to any disclaimer, the term of this patent is extended or adjusted under 35 U.S.C. 154(b) by 0 days.

(21) Appl. No.: 09/486,772

(22) PCT Filed: Aug. 26, 1998

(86) PCT No.: PCT/EP98/05504

§ 371 Date: Feb. 28, 2000

§ 102(e) Date: Feb. 28, 2000

(87) PCT Pub. No.: WO99/11607

PCT Pub. Date: Mar. 11, 1999

(30) Foreign Application Priority Data

Aug. 28, 1997 (CH) .................................. 2022/97

(51) Int. Cl.⁷ ................................................. C07C 255/00
(52) U.S. Cl. ............................................................. 558/405
(58) Field of Search ............................................. 558/405

(56) References Cited

FOREIGN PATENT DOCUMENTS

WO 93 19750   10/1993   (WO).

OTHER PUBLICATIONS

Kazuo Haga et al. "Condensations of 1,4–Cyclohexanediones and Secondary Aromatic Amines. The Formation of Alkyldiarylamines and Triarylamines", Bulletin of the Chemical Society of Japam, vol. 57, No. 6, pp. 1586–1590, Jun. 1984.

*Primary Examiner*—Joseph K. McKane
*Assistant Examiner*—Joseph Murray
(74) *Attorney, Agent, or Firm*—James M. Kanagy; Charles M. Kinzig

(57) ABSTRACT

This invention relates to a process for converting isovanillin to substituted 4-cyano-4-(3,4-disubstitutedphenyl) cyclhexanones. These ketones are useful in preparing certain PDE4 ingibitors wherein the 1-postion keto group is converted to a carboxylic acid group.

6 Claims, No Drawings

METHOD FOR PRODUCING A 1-(3-CYCLOPENTENYLOXY-4-ALKOXYPHENYL)-4-OXOCYCLOHEXANECAR-BONITRILE

This is a 371 of international Application PCT/EP98/05504, filed Aug. 26, 1998.

The present invention concerns a new process for production of a 1-(3-cyclopentyloxy-4-alkoxyphenyl)-4-oxocyclohexanecarbonitrile starting from 4-cyano-4-(3-cyclopentyloxy-4-methoxyphenyl)heptanediacid dialkyl ester.

1-(3-cyclopentyloxy-4-alkoxyphenyl)-4-oxocyclohexanecarbonitrile, abbreviated CMC below, is used in the manufacture of pharmaceuticals, for example in the production of phenylcyclohexane-1-ylcarboxylic acid derivatives, which inhibit the production of tumor necrosis factor (WO 95/24381).

There are several known processes for production of CMC. For example, WO 95/24381 describes a 4-stage procedure for production of CMC that begins with 3-cyclopentyloxy-4-methoxybenzaldehyde. In this procedure, 3-cyclopentyloxy-4-methoxybenzaldehyde is converted into 3-cyclopentyloxy-4-methoxyphenylacetonitrile, which with Triton-B and methyl acrylate is turned into the 4-cyano-4-(3-cyclopentyloxy-4-methoxyphenyl)heptanediacid dimethyl ester. The latter, in the presence of a strong base, is then cyclized into 5-cyano-5-(3-cyclopentyloxy-4-methoxyphenyl)-2-oxocyclohexanecarboxylic acid methyl ester, which upon dissolution in dimethyl sulfoxide is decarboxylated to form CMC. With this procedure, CMC is obtained through a quite involved process with several changes of solvent at a yield of approximately 60% relative to 4-cyano-4-(3-cyclopentyloxy-4-methoxyphenyl)heptanediacid dimethyl ester, which is abbreviated as CMD below. The two disadvantages of this procedure are the mediocre yield and the use of dimethyl sulfoxide (DMSO) in an environment in which the solvent is inclined to thermal decomposition.

The goal of the present invention was to provide a simpler process for the production of CMC in which the desired product is isolated with good yields.

This goal is achieved with the process according to claim 1. According to the invention, the process is carried out such that CMD, of the general formula

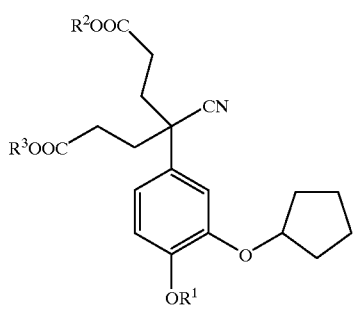

II wherein $R^1$, $R^2$ and $R^3$ represent $C_{1-5}$-alkyl groups, is cyclized in the presence of a base to a 5-cyano-5-(3-cyclopentyloxy-4-alkoxyphenyl)-2-oxocyclohexanecarboxylic acid alkyl ester, abbreviated CMOM below, of the general formula

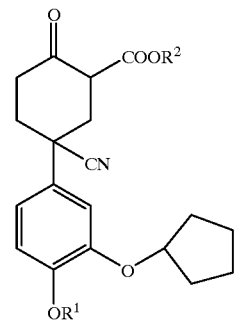

III wherein $R^1$ and $R^2$ have the given meaning, the compound of the general formula III is neutralized with an alkali metal hydrogen carbonate, and is then decarboxylated in the presence of an alkali metal carbonate to form the end product of formula I.

$C_{1-5}$-alkyl can be defined below as methyl, ethyl, propyl, isopropyl, butyl, tert-butyl and pentyl.

An alkali metal hydride or an alkoxide [1] may be used as base. Examples of alkoxides that can be used include alkali metal alkoxides such as sodium or potassium methoxide, sodium or potassium ethoxide, sodium or potassium propoxide, or sodium or potassium butoxide. Sodium hydride, for example, may be used as the alkali metal hydride.

Sodium or potassium hydrogen carbonate may be used as the alkali metal hydrogen carbonate.

It is expedient to carry out the cyclization of the CMD to the CMOM at a temperature of 20 to 100° C., preferably from 50 to 70° C. The decarboxylation of the CMOM to the CMC is efficiently conducted at a temperature of 20 to 100° C., preferably from 70 to 90° C.

It is expedient to carry out the decarboxylation under weakly basic conditions, preferably between pH 8 and pH 12.

Polar solvents such as ether may be used as the solvent for the cyclization and decarboxylation. Dioxane, diethyl ether, dibutyl ether, anisole, tetrahydrofuran or mono-, di-, tri- or polyethyleneglycol ether, such as 1,2-dimethoxyethane may be used as the ether.

The production of the educt, the CMD of general formula II, is known in principle from PCT WO 93/19 750. It is expedient to produce the CMD of general formula II such that in a first stage, an isovanillin derivative of the general formula

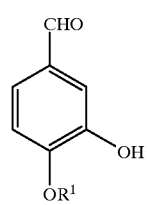

IV wherein $R^1$ has the given meaning, is reacted with a halogen cyclopentane to form a 3-cyclopentyloxy-4-methoxybenzaldehyde of the general formula

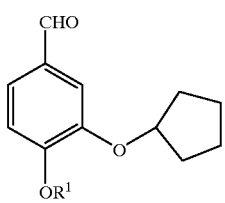

wherein $R^1$ has the given meaning.

It is expedient to conduct the conversion in the first stage in the presence of an alkali metal or earth alkaline metal carbonate. Sodium or potassium carbonate may be used as the alkali metal carbonate and magnesium or calcium carbonate may be used as the earth alkaline metal carbonate.

Fluoro-, chloro-, bromo- or iodocyclopentane may be used as the halogen cyclopentane.

The conversion in the first stage is efficiently conducted in a polar solvent. Examples of polar solvents that may be used include dimethylformamide (DMF) or a $C_{1-4}$-alcohol such as methanol, ethanol, propanol or butanol. Methanol is preferable.

The conversion in the first stage is effectively conducted at a temperature of 100 to 130° C., preferably 110 to 125° C.

In the second stage, the 3-cyclopentyloxy-4-methoxybenzaldehyde is reduced to the (3-cyclopentyloxy-4-methoxyphenyl)methanol of the general formula

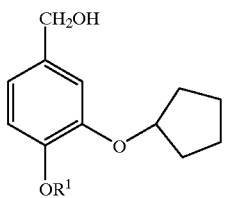

The reduction is efficiently conducted with sodium or potassium borohydride.

It is expedient to carry out the reduction in the second stage at a temperature of −10 to 90° C., preferably 0 to 25° C.

The reduction is usually conducted in an atmosphere of inert gas. The same solvents used in the first stage may be used here.

In the third stage, the (3-cyclopentyloxy-4-methoxyphenyl)methanol is halogenated to a 4-(halogenmethyl-2-cyclopentyloxy-1-alkoxy)benzene of the formula

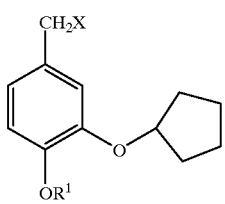

Hydrogen chloride or bromide, especially an aqueous solution of hydrogen chloride or bromide, may be used as the halogenation agent. Hydrogen chloride is preferable.

It is expedient to conduct the halogenation in an atmosphere of inert gas in a hydrocarbon solvent. Toluene, xylol or benzene may be used as the hydrocarbon.

It is expedient to conduct the halogenation at a temperature of 0 to 50° C., preferably 10 to 25° C.

In the fourth stage, the (halogenmethyl-2-cyclopentyloxy-1-alkoxy)benzene is converted into a (3-cyclopentyloxy-4-alkoxyphenyl)acetonitrile of the general formula

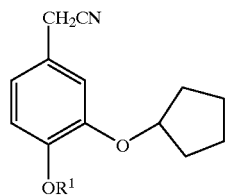

wherein $R^1$ has the given meaning.

The conversion in the fourth stage is effectively conducted in an atmosphere of inert gas and in a polar solvent. The same solvents used in the first and the second stages may be used as the polar solvent.

The fourth stage is usually carried out with an alkali metal cyanide such as sodium or potassium cyanide.

The conversion in the forth stage is effectively carried out at a temperature of 10 to 100° C., preferably 20 to 50° C.

In the fifth stage, the (3-cyclopentyloxy-4-alkoxyphenyl)acetonitrile is combined with an alkyl acrylate to form the CMD of the general formula

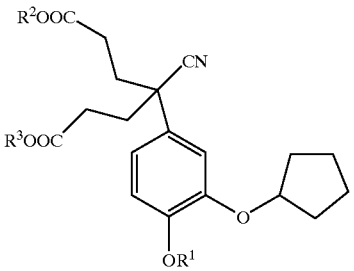

Methyl, ethyl, propyl or butyl acrylate may be used as the alkyl acrylate.

The conversion in the fifth stage is effectively carried out in the presence of a base, as for example in the presence of a non-ionic tenside such as Triton B.

The conversion in the fifth stage may be conducted in a polar solvent. Acetonitrile and DMF are suitable polar solvents.

The conversion in the fifth stage is effectively conducted at a temperature of 0 to 60° C., preferably 20 to 40° C.

The inventive process for production of CMC of the general formula I is simple to carry out due to the few required solvent changes and delivers the desired product at a yield of 70 to 80%.

EXAMPLE 1

Production of (3-cyclopentyloxy-4-methoxyphenyl)methanol 800 g DMF, 140 g (0.916 mol) isovanillin, 254 g (1.831 mol) potassium carbonate and 193 g (1.825 mol) chlorocyclopentane were combined and heated to 120–125° C. After 3 h, the mixture was cooled to 25° C., filtered and washed with 508 g methanol. The filtrate was cooled to 0–5° C. and mixed in 4 portions within 1 h at 0–15° C. with 10.8 g sodium borohydride. Thirty minutes after this mixing ended, the mixture was warmed to 25–30° C. and stirred at this temperature for 2 h. The mixture was then cooled to 10–15° C. and 63 g hydrochloric acid (19.5%) was added to it over 20 minutes. Then the majority of the solvent was distilled off under vacuum. One then added 1,160 g water and 1,036 g toluene to the residue, stirred for 5 min and removed the lower water phase. The extraction was repeated twice with a total of 995 g E-water[1]. 1,230.9 g organic phase were obtained (assay 15.61 weight-% (3-cyclopentyloxy-4-methoxyphenyl)methanol, GC with internal standard). Yield: 94.4% relative to isovanillin

EXAMPLE 2

Production of (4-chloromethyl-2-cyclopentyloxy-1-methoxy)benzene 327.8 g (3-cyclopentyloxy-4-methoxyphenyl)methanol solution in toluene (produced from 0.356 mol isovanillin) were put into a flask made inert with $N_2$ at 21.5° C. Over 1 hour, 105.5 g 32% HCl (0.926 mol) was added by drops so that the temperature remained below 25° C. The reaction mixture was diluted with 110 g toluene and the phases were separated. The organic phase was mixed with 10 g solid $NaHCO_3$, stirred for 10 min and filtered. The filtrate was concentrated. 94.1 g (4-chloromethyl-2-cyclopentyloxy-1-methoxy)benzene was obtained in crude form as a brown oil.

EXAMPLE 3

Production of (3-cyclopentyloxy-3-methoxyphenyl) acetonitrile 85.16 g of crude (4-chloromethyl-2-cyclopentyloxy-1-methoxy)benzene (produced from 0.364 mol isovanillin) and 230 g DMF were put into a flask made inert with $N_2$ at 21° C. 10.7 g NaCN were added to the clear solution. The temperature rose to 28.5° C. within 1 hour. Then another 10.7 g NaCN were added. The reaction mixture was stirred for another hour and then heated to 50° C. over 30 min. After stirring for another 1.5 h at 50° C., the solvent was distilled off as completely as possible. The residue was extracted with 365 g toluene and 125 g water. The organic phase was concentrated under vacuum. 78.5 g of crude (3-cyclopentyloxy-3-methoxyphenyl)acetonitrile were obtained in the form of brown oil (assay by GC with internal standard: 89.3%). Yield: 83.3% relative to isovanillin.

EXAMPLE 4

Production of CMD 82.2 g of crude (3-cyclopentyloxy-3-methoxyphenyl) acetonitrile (assay: 89.0%, 0.316 mol), 406 g acetonitrile and 1 g water were put into a flask made inert with $N_2$ at 21° C. A solution of 94 g methyl acrylate (1.092 mol) in 54.5 g acetonitrile was prepared in a dropping funnel; a solution of 12.72 g 35% methanolic benzyltrimethyl ammonium hydroxide solution (Triton-B) (containing approximately 5% water) in 54.5 g acetonitrile was prepared in another dropping funnel. At 21° C., ¼ of the methyl acrylate solution was added, then ⅓ of the Triton-B solution was added (exothermic reaction: the temperature climbed immediately to 38° C.). After cooling to 20° C. over 15 min, another ¼ of the methyl acrylate solution was added, followed 10 min later by ⅓ of the Triton-B solution (immediate temperature rise to 34° C.). The mixture was then cooled to 20° C. over 15 min. After 10 min., another ¼ of the methyl acrylate solution was added, followed 10 min. later by ⅓ of the Triton-B solution (temperature rise to 25° C.). The mixture was then cooled to 20° C. over 10 min. After 10 min., the remainder of the methyl acrylate was added, followed 10 min. later by ⅓ of the Triton-B solution, with the remainder of the Triton-B added 5 min. after that. The reaction mixture was stirred for 1.5 h at 23° C. The brown solution was concentrated. The residue was partitioned between 430 g methylcyclohexane and 56 g water at 80° C. The organic phase was washed at the same temperature with 56 g water and then concentrated. The residue (clear brown solution) was cooled to 0° C. while being stirred and stirred for 1 h at 0° C. The product was vacuum filtered and washed twice with a little cold methylcyclohexane, then dried. 111.2 g crystalline CMD were obtained. Yield: 87.2% relative to (3-cyclopentyloxy-3-methoxyphenyl)acetonitrile

EXAMPLE 5

Production of CMOM 33.98 g (82 mmol) CMD (97%) were dissolved in 90 g dioxane and mixed at room temperature with 18.75 g (104 mmol) 30% sodium methoxide. The solution was heated to reflux temperature over 20 min. After 30 min., practically all of the educt was converted (as confirmed by thin-layer chromatography) and one began to draw off the distillate. A total of 26.4 g distillate were removed in 90 min. The solution was cooled to 60° C., resulting in an easily stirred, beige suspension. 10.03 g (119 mmol) sodium bicarbonate and 100 g water were added to the suspension, yielding a mixture with two almost clear phases. This was taken directly into the next stage.

EXAMPLE 6

Production of CMC

Approximately 253 g reaction mixture from the previous stage were heated to reflux. This was stirred for a total of 10 h with a bath temperature of 110° C. and an internal temperature of 87° C. Thin-layer chromatography confirmed that the conversion was complete at this time. A total of 104 g distillate were drawn off from this 2-phase mixture. A mixture of 124 g (161 ml) methylcyclohexane and 14 g (16 ml) ethyl acetate was added to the easily stirred suspension after it had been cooled to 85–90° C. At a reactor temperature of 90° C. and with slow reflux, the clear water phase was drained off and the yellow organic phase was washed at the same temperature with 80 g water (in two portions). The organic phase was cooled to 0° C. over 1 h. After 1 h at 0° C., this phase was filtered, the residue washed with 80 ml methylcyclohexane/ethyl acetate 9:1 (w/w, cold) in two portions, and dried (approximately 4 h, 20 mbar, 55° C.). 17.91 g crystallized product were obtained with a content of 98.9% (HPLC). The mother liquor was evaporated and dried, yielding 2.99 g product with a CMC content of 62.7%. Yield: 17.91 g product with a content of 98.9% was equivalent to 56.5 mmol=69% yield relative to initial quantity of CMD (i.e. over both stages). The total yield of CMC thus formed was 77%.

SUMMARY

A new process is described for production of 1-(3-cyclopentyloxy-4-alkoxyphenyl)-4-oxocyclohexanecarbonitrile of the general formula In this process, a 4-cyano-4-(3-cyclopentyloxy-4-methoxyphenyl)-heptanediacid dialkyl ester of the general formula

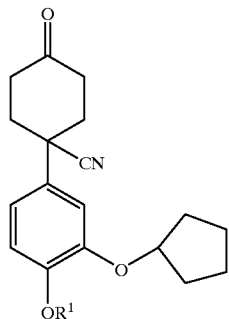

I

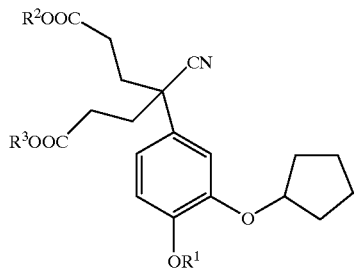

II is cyclized in the presence of a base to a 5-cyano-5-(3-cyclopentyloxy-4-alkoxyphenyl)-2-oxocyclohexanecarboxylic acid alkyl ester of the general formula

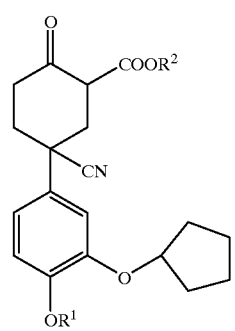

III then the compound of the general formula III is neutralized with an alkali metal hydrogen carbonate and this product is then decarboxylated in the presence of an alkali metal carbonate to form the end product as per formula I.

What is claimed is:

1. Process for production of a 1-(3-cyclopentyloxy-4-alkoxyphenyl)-4-oxocyclohexanecarbonitrile of the general formula

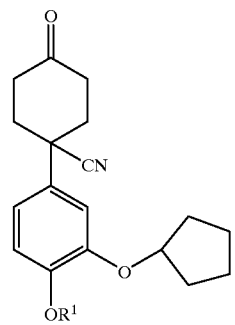

I wherein $R^1$ signifies a $C_{1-5}$-alkyl group, comprising the cyclization of a 4-cyano-4-(3-cyclopentyloxy-4-methoxyphenyl)heptanediacid dialkyl ester of the general formula

II wherein $R^1$ has the given meaning and $R^2$ and $R^3$ signify $C_{1-5}$-alkyl groups, in the presence of a base, to a 5-cyano-5-(3-cyclopentyloxy-4-alkoxyphenyl)-2-oxocyclohexanecarboxylic acid alkyl ester of the general formula

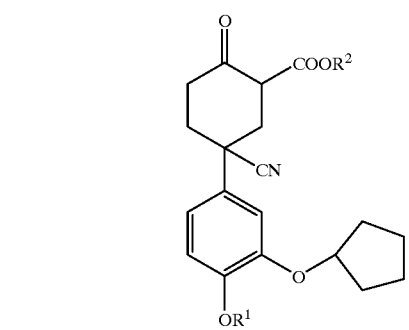

III wherein $R^1$ and $R^2$ have the given meanings, neutralization of the compound to the general formula III with an alkali metal hydrogen carbonate and then decarboxylation, in the presence of an alkali metal carbonate, to the end product as per formula I.

2. Process according to claim 1, whereby one uses an alkali metal alkoxide as base for the cyclization.

3. Process according to claim 1, whereby one conducts the decarboxylation under weakly basic conditions.

4. Process according to claim 1, whereby one carries out the cyclization and the decarboxylation in a polar solvent.

5. Process according to claim 4, whereby one uses an ether as the polar solvent.

6. Process according to claim 1, whereby the 4-cyano-4-(3-cyclopentyloxy-4-methoxyphenyl)heptanediacid dialkyl ester of the general formula II, wherein $R^1$, $R^2$ and $R^3$ have the given meanings, is produced such that in a first stage, an isovanillin derivative of the general formula

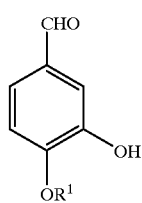

IV wherein R¹ has the given meaning, is converted with a halogen cyclopentane into a 3-cyclopentyloxy-4-alkoxybenzaldehyde of the general formula

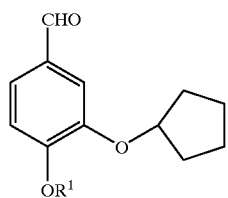

V wherein R¹ has the given meaning, and this product is reduced in a second stage to a (3-cyclopentyloxy-4-alkoxyphenyl)methanol of the general formula

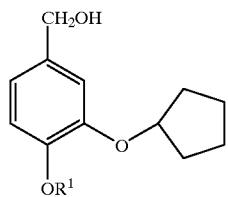

VI wherein R¹ has the given meaning, and this product is halogenated in a third stage to a 4-(halogenmethyl-2-cyclopentyloxy-1-alkoxy)benzene of the general formula

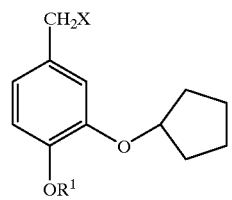

VII wherein R¹ has the given meaning and X signifies a halogen atom, and this product is then converted in a fourth stage into a (3-cyclopentyloxy-4-alkoxyphenyl)acetonitrile of the general formula

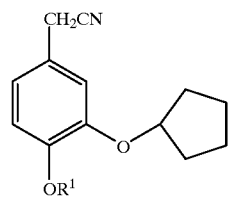

VIII wherein R¹ has the given meaning, and finally this product is converted in the fifth stage with an alkyl acrylate into 4-cyano-4-(3-cyclopentyloxy-4-alkoxyphenyl)heptanediacid dialkyl ester of the general formula II.

* * * * *